United States Patent [19]

Machi

[11] Patent Number: 5,446,379
[45] Date of Patent: Aug. 29, 1995

[54] METHOD AND SYSTEM FOR SEARCHING AND SENSING REINFORCING STEEL IN CONCRETE BY EMPLOYING AN OSCILLATOR DRIVER SENSOR COIL

[75] Inventor: Yoshio Machi, Kosigaya, Japan

[73] Assignee: Nishimatsu Construction Co. Ltd., Tokyo, Japan

[21] Appl. No.: 825,940

[22] Filed: Jan. 27, 1992

[30] Foreign Application Priority Data

Aug. 28, 1991 [JP] Japan .................................. 3-296705
Oct. 31, 1991 [JP] Japan .................................. 3-311578

[51] Int. Cl.⁶ ..................... G01N 27/87; G01R 33/12
[52] U.S. Cl. ...................... 324/240; 324/207.17; 324/207.22; 324/207.26
[58] Field of Search ............ 324/207.14, 207.26, 324/207.22, 239–243, 236–238, 67, 326, 207.17, 207.11

[56] References Cited

U.S. PATENT DOCUMENTS

| | | | |
|---|---|---|---|
| 2,970,256 | 1/1961 | Sazynski et al. | 324/240 |
| 4,035,721 | 7/1977 | Lorenzi et al. | 324/240 X |
| 4,438,754 | 3/1984 | Nanny et al. | 324/243 X |
| 4,531,091 | 7/1985 | Kasenberger et al. | 324/243 X |
| 4,837,509 | 6/1989 | Dodmann et al. | 324/207.14 |
| 4,868,504 | 9/1989 | Johnson | 324/239 X |
| 4,931,730 | 6/1990 | Olsen et al. | 324/240 X |

*Primary Examiner*—Sandra L. O'Shea
*Assistant Examiner*—Warren S. Edmonds
*Attorney, Agent, or Firm*—Rosen, Dainow & Jacobs

[57] ABSTRACT

A system for searching and sensing reinforcing steel in reinforced concrete is provided. The system comprises a means for magnetizing the reinforcing steel in the reinforced concrete with lines of magnetic force generated by a magnetic field and a means for sensing the lines of magnetic force radiated from the magnetized reinforcing steel to detect an existence and a condition of the reinforcing steel in the reinforced concrete. The sensing means includes a coil for sensing a magnetic force and the magnetizing means is positioned remote from the sensing means.

28 Claims, 8 Drawing Sheets

METHOD AND SYSTEM FOR SEARCHING AND SENSING REINFORCING STEEL IN CONCRETE BY EMPLOYING AN OSCILLATOR DRIVER SENSOR COIL

BACKGROUND OF THE INVENTION

1. Field of the Invention

This invention relates to improvements in a method and a system for searching for a reinforcing steel in a reinforced concrete, employed in the construction and building business and the authorities concerned, and more particularly to such a method and a system in which the reinforcing steel in the concrete is magnetized prior to a searching operation in order to greatly improve the sensitivity of detection.

2. Description of the Prior Art

Hitherto, three typical techniques set forth hereinafter have been proposed and known to search the reinforcing steel in the reinforced concrete.

Figure 15:
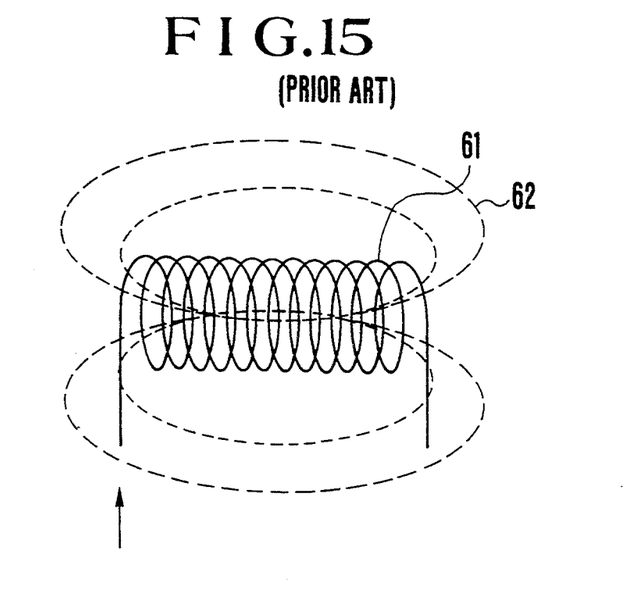
FIG. 15 is an explanatory view showing the operational principle of a conventional technique.

(1) First conventional technique:

As shown in FIG. 15, a reinforcing steel searching instrument includes a sensor having a simple coil 61, in which an alternating current is passed through the coil 61 to generate lines of magnetic force which are formed through the opposite ends of the coil 61. This coil 61 is approached as the sensor to the surface of a concrete wall, in which a change is made in the lines of magnetic force if a reinforcing steel as a magnetic material exists in the concrete wall. This change is converted to a voltage or a current which is indicated in a visible manner in an indicator, thereby searching the existence of the reinforcing steel in the concrete.

Figure 16:
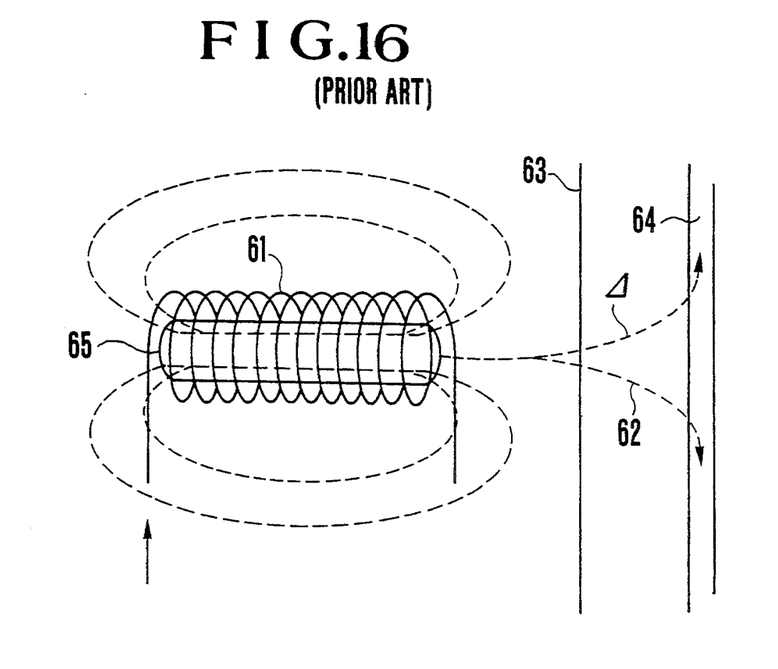
FIG. 16 is an explanatory view showing the operational principle of another conventional technique.

(2) Second conventional technique:

As shown in FIG. 16, a reinforcing steel searching instrument includes a sensor having a core 65 which is made of a magnetic material and disposed inside the coil 61. Upon passing current through the coil 61, uniform lines of magnetic force is developed at the opposite ends of the core 65. The lines of magnetic force are radiated from the end of the core 65 and converged to the opposite end of the core. The sensor is encased to form a probe which is approached to and moved on the surface of a concrete structure 63 to search a location at which the lines of magnetic force are concentrated. If the reinforcing steel 64 is present there, the indication of a meter changes so that the location of the reinforcing steel is nearly determined. This conventional technique is slightly higher in sensitivity and precision of detection than the first conventional technique because of provision of the core 65 inside the coil 61 of the probe.

(3) Third conventional technique

This is a technique using a reinforcing steel searching instrument including a resonance circuit, as disclosed in Japanese Patent Provisional Publication No. 2-49187. In this instrument, a voltage at a predetermined frequency output from an oscillator is supplied to two circuit systems. One of the circuit systems includes a resonance circuit having a sensor coil and a variable capacitor, and an amplifier, whereas the other includes a phase converter connected in parallel with the resonance circuit, and an amplifier. The outputs from the two circuit systems are input to a differential amplifier to compare and amplify the outputs. The result of such comparison and amplification is input to a lock-in amplifier to pick up the output having the same frequency as the output frequency of the oscillator.

With this conventional arrangement, in case the sensor coil is used as a sensor or probe, the existence of the reinforcing steel is represented as an output differential between the two circuit systems. As a result, this technique is high in detection sensitivity and searchable depth of location of the objective reinforcing steel in the concrete, as compared with the first and second conventional techniques.

However, difficulties have been encountered in the above three conventional techniques as follows:

In the first conventional technique, since a sensor element consists of only the coil, the generated magnetic flux is not only weak but also spreaded laterally from the opposite ends of the coil, so that the magnetic flux is thin near the reinforcing steel to be searched, thereby lowering the sensitivity and precision of detection.

In the second conventional technique, the magnetic flux radiated from the core 65 extends generally in the axial direction of the core 65, so that the sensor unnecessarily senses a magnetic material located rearward of the sensor or probe. As a result, the resolution of the object to be searched is relatively low, and therefore this conventional technique is also low in sensitivity and precision of the detection.

In the third conventional technique, since the resonance circuit is used, the sensitivity and precision of detection is higher than the first and second conventional techniques. However, detection of the searching instrument of this conventional technique only depends upon a change in magnetic flux in the sensor coil which change is caused by the existence of the reinforcing steel in the concrete. It is to be noted that this change is considerably delicate, so that the sensitivity and precision of detection is unavoidably suppressed at a low value.

As will be understood from the above, the reinforcing steel searching instruments of the three conventional techniques never employ a new technique of magnetizing the reinforcing steel embedded in the concrete, before the detection operation of the reinforcing steel searching instrument.

The principle of operation of the above conventional techniques will be discussed. First, the sensor coil 61 is represented generally as shown in FIGS. 15 and 16. The self inductance $L_1$ of the sensor coil 61 is given by Eq. 1.

$$L_1 = \Phi_1 / I_1 N_1 \qquad \text{(Eq. 1)}$$

where $I_1$ is current to the coil; $N_1$ is the number of turns of the coil; and $\Phi_1$ is the magnetic flux.

The operational relationship between the coil 61 and the reinforcing steel 64 (not magnetized) is represented in FIG. 16, in which the magnetic flux 62 absorbed into the reinforcing steel 64 is indicated by $\Delta$ (delta). As a result of this operation, the self inductance $L_1'$ of the coil 61 is changed and given by Eq. 2.

$$L_1' = (\Phi_1 - \Delta)/I_1 N_1 \qquad \text{(Eq. 2)}$$

Thus, in the conventional techniques in which no magnetization of the reinforcing steel is carried out, the self inductance of the sensor coil is suppressed at a low value, and therefore the electromotive force at the sensor coil is considerably small thereby lowering the sensitivity and precision of detection of the embedded reinforcing steel in the concrete. Accordingly, the above-discussed or other conventional techniques for searching the reinforcing steel in the concrete are low in sensitivity and precision of the detection, and additionally such low in searchable depth of the reinforcing steel in the concrete as only 5 to 6 cm. This makes considerable troubles for the business world of constructors and builders and the authorities concerned.

SUMMARY OF THE INVENTION

It is an object of the present invention to provide an improved method and system for searching for the reinforcing steel embedded in reinforced concrete, which can overcome drawbacks encountered in conventional corresponding techniques.

Another object of the present invention is to provide an improved method and system for searching for the reinforcing steel in concrete, which is highly improved in sensitivity and precision of detection of the reinforcing steel, while greater enlarging the searchable depth of location of the embedded reinforcing steel in the concrete.

An aspect of the present invention is a method for searching a reinforcing steel in a reinforced concrete, comprised of the following steps: A first step of magnetizing the reinforcing steel in the reinforced concrete with lines of magnetic force generated by a magnetic field; and a second step of sensing the lines of magnetic force radiated from the magnetized reinforcing steel to detect an existence and a condition of the reinforcing steel in the reinforced concrete by using a reinforcing steel searching instrument having a coil for sensing a magnetic force.

Another aspect of the present invention is a system for searching a reinforcing steel in a reinforced concrete, comprised of a magnetizing device of magnetizing the reinforcing steel in the reinforced concrete with lines of magnetic force generated by a magnetic field. Additionally, a reinforcing steel searching instrument is provided to sense the lines of magnetic force radiated from the magnetized reinforcing steel to detect an existence and a condition of the reinforcing steel in the reinforced concrete, the instrument including a coil for sensing a magnetic force.

With the thus arranged method and system, the reinforcing steel embedded in the concrete is searched or detected by the magnetic force sensing coil type searching instrument after the reinforcing steel is magnetized. As a result, the sensitivity and precision of detection of the reinforcing steel is largely improved while greatly enlarging the searchable depth of location of the reinforcing steel, over a variety of conventional techniques.

BRIEF DESCRIPTION OF THE DRAWINGS

In the drawings, like reference numerals designate like elements and parts throughout all the figures, in which.

DETAILED DESCRIPTION OF THE INVENTION

According to the present invention, a method for searching a reinforcing steel in a reinforced concrete is comprised of the following steps: A first step of magnetizing the reinforcing steel in the reinforced concrete with lines of magnetic force generated by a magnetic field; and a second step of sensing the lines of magnetic force radiated from the magnetized reinforcing steel to detect an existence and a condition of the reinforcing steel in the reinforced concrete by using a reinforcing steel searching instrument having a coil for sensing a magnetic force.

Thus, in accordance with the reinforcing steel searching method of the present invention, the existence, thickness (diameter), number and the like of the reinforcement steel embedded in the reinforced concrete can be searched by accomplishing the above-mentioned two steps. In general, magnetization of a magnetic material has been hitherto carried out in magnetization of a iron piece in a variety of meters. However, it is to be noted that magnetization of the reinforcing steel in the reinforced concrete has not yet been hitherto carried out.

According to the method of the present invention, at the first step, a direct current magnetic field is formed in the reinforcing steel in the reinforced concrete by using a magnetizing device which is a permanent magnet or one generating a direct current, prior to searching the reinforcing steel in the reinforced concrete. Otherwise, an alternating current magnetic field may be formed in the reinforcing steel by using an alternating current in order to magnetize the reinforcing steel. At this first step, a probe (including a sensor for sensing the magnetic force) of the reinforcing steel searching instrument is located far from the magnetizing device, so that the sensor is not affected by the magnetic field of the magnetizing device. When the magnetizing device such as the magnet for forming the magnetic field is approached to the surface of the concrete, the reinforcing steel is magnetized if any. In case of magnetization by the direct current magnetic field or if the depth-location (location from the surface of the concrete) of the reinforcing steel is large even in case of magnetization by the alternating current magnetic field, the magnetization is weak in which the degree of amplification for a detection signal in the searching instrument is raised so as to effectively search for the reinforcing steel.

When the reinforcing steel is magnetized, the line of magnetic force is radiated from the magnetized reinforced steel. At the second step, the line of magnetic force is sensed by the sensor which is of a so-called passive type or a so-called active type. The passive type sensor is adapted to sense only the line of magnetic force radiated from the magnetized reinforcing steel. The active type sensor is adapted to detect the mutual effect between the line of magnetic force radiated from the magnetized reinforcing steel and the line of magnetic force radiated from a sensor coil of the probe. In either case, the result of such a detection can be indicated in an indicating meter of the searching instrument, in which the active type sensor is higher in sensitivity and precision than the passive type one.

It will be understood that the reinforcing steel has been already slightly magnetized during production or cutting. However, by positively magnetizing the reinforcing steel by using the direct current magnetic field as discussed above, the magnetic force of the reinforcing steel or the output of the sensor is increased about 10 times as compared with the conventional techniques in which no positive magnetization is made. If the direct magnetic field is further strengthened, it will be expected that the magnetic force of the reinforcing steel can be further increased. In case of magnetization by the alternating current magnetic field, the magnetic field of the reinforcing steel or the output of the sensor is increased about 30 times as compared with the conventional techniques, in which the magnetic field of the reinforcing steel can be further increased.

In case that the frequency of an oscillator in a measuring system or the searching instrument is coincided with the frequency of the line of magnetic force radiated from the reinforcing steel magnetized by the alternating current magnetic field, a so-called synchronizing detection is made in which a high sensitivity and precision detection can be made even if the reinforcing steel: is weak in magnetism and located deep in the concrete. Additionally, even in case of detection for two adjacent reinforcing steels, a high sensitivity and precision detection can be made by magnetizing either one of them, or otherwise by magnetizing them respectively with reverse polarities N and S.

Next, the principle of the present invention will be discussed with reference to FIG. 1.

Figure 1:
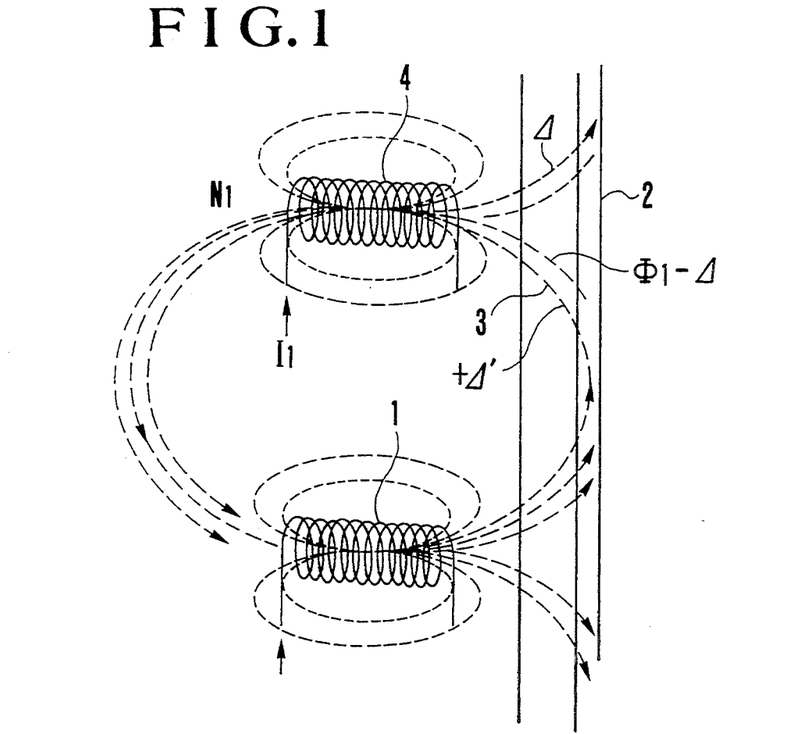
Fig. 1 is an explanatory view showing the principle of the present invention.

An explanatory illustration of FIG. 1 shows a state of mutual inductance between a magnetizing coil 1 of the magnetizing device and a sensor coil 4 in the searching instrument. When the reinforcing steel 2 is magnetized by the magnetizing coil 1, the magnetized reinforcing steel generates a magnetic flux of $+\Delta$ which reaches the sensor coil 4. Then, the magnetic flux becomes $(\Phi_1 - \Delta + \Delta')$ which is higher by $\Delta'$ as compared with the corresponding magnetic flux $(\Phi_1 - \Delta)$ in the above-discussed conventional technique in which the reinforcing steel is not magnetized.

In case that the sensor coil 4 is incorporated in a resonance circuit and that the line of magnetic force comes from the reinforcing steel, the inductance of the sensor coil functions as a mutual inductance, and therefore the inductance $L_1''$ of the sensor coil 4 is given by Eq. 3.

$$L_1'' = (\Phi_1 - \Delta + \Delta')/I_1 N_1 \quad \text{(Eq. 3)}$$

Figure 2:
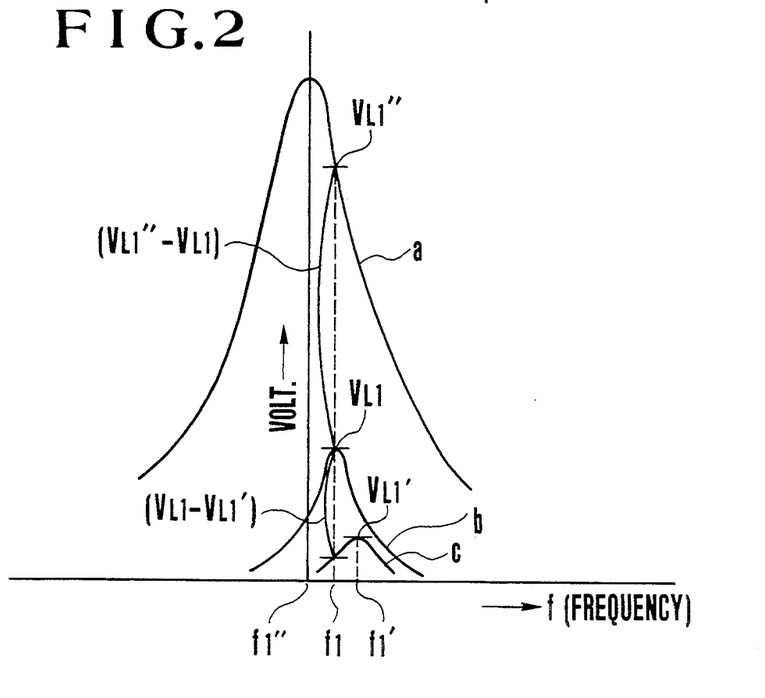
FIG. 2 is a graph showing effects according to the principle of the present invention.

Accordingly, the resonance circuit including the sensor coil 4 has a resonance characteristics as indicated by a curve a in FIG. 2. It will be understood that $\Delta'$ can be sufficiently enlarged by increasing the magnetic force of the magnetizing coil I upon such incorporation of this sensor coil 4 in the resonance circuit. As a result, the inductance $L_1''$ can be sufficiently enlarged as compared with the inductance $L_1'$ in case that the reinforcing steel is not magnetized.

In connection with the resonance circuit including the sensor coil, in case that there is no reinforcing steel, the resonance circuit exhibits the characteristics as indicated by a curve b in FIG. 2, in which the voltage $V_{L1}$ at the terminals of the sensor coil 4 becomes the maximum at the resonance frequency $f_1$. In case that the sensor coil 4 is approached toward the reinforcing steel without previously using the magnetizing coil, the inductance $L_1'$ of the sensor coil 4 becomes as given by Eq. 4.

$$L_1' = (\Phi_1 - \Delta)/I_1 N_1 \quad \text{(Eq. 4)}$$

Accordingly, resonance is made under the action of the same capacitor C as in the resonance circuit, in which the resonance frequency $f_1'$ obtained under the action of $L_1'$ (in case of using no resonance circuit and no magnetizing coil) and C is given by Eq. 5.

$$f_1' = 1/\{2\pi(L_1'C)^{\frac{1}{2}}\} \quad \text{(Eq.5)}$$

The resonance characteristics in connection with this resonance frequency is indicated by a curve c in FIG. 2 in which a resonance is made at the frequency $f_1'$ higher than $f_1$. Consequently, upon such shifting of the resonance frequency, the voltage at the, terminals of the sensor coil 4 at the frequency $f_1$ is lowered, detection of the reinforcing steel is carried out under the action of difference between $V_{L1}$ and $V_{L1}'$ (the voltage at the terminals of the sensor coil at the frequency $f_1$).

In contrast, according to the present invention, the self inductance $L_1''$ of the sensor: coil 4 can be enlarged by an amount $\Delta'$ by using the magnetizing coil 1, and therefore the resonance frequency $f_1$ under the action of the same capacitor C for resonance shifts to a point of $f_1''$ as shown in FIG. 2. Consequently, the voltage $V_{L1}''$ is given by Eq. 6.

$$V_{L1}'' = j\omega L_1'' \cdot I_1 \quad \text{(Eq. 6)}$$

where j is a complex number; and $\omega$ is an angular frequency.

This voltage ($V_{L1}''$ is much higher than the voltage $V_{L1}$, so that a value ($V_{L1}'' - V_{L1}$) is larger than a value ($V_{L1} - V_{L1}'$). As a result, the searching instrument or detector indicates a high output value at $V_{L1}''$ as compared with an output value at $V_L'$. This demonstrates that the searching or detecting precision is very high in the method (according to the present invention) in which the detection of the reinforcing steel is made after magnetization of the reinforcing steel, as compared with that in the conventional technique in which no magnetization is made to the reinforcing steel.

Preferably, the reinforcing steel searching instrument used to carry out the present invention is arranged as follows: An oscillator for generating a predetermined high frequency voltage signal. A first resonance circuit (serving as a sensor) is connected in series with the oscillator and including a magnetic force sensing coil and a first variable capacitor. The first resonance circuit is adapted to input the voltage signal having a frequency around a resonance frequency and output a second voltage signal representative of a change in inductance caused upon the approach of the magnetic force sensing coil to the reinforcing steel. A second resonance circuit (serving as a reference circuit) is connected in series with the oscillator and in parallel with the first resonance circuit. The second resonance circuit includes a coil and a second variable capacitor which are equally rated respectively with the magnetic force sensing coil and the first variable capacitor. A differential amplifier is connected to the first and second resonance circuits to calculate a difference in output between the first and second resonance circuits. A lock-in amplifier is connected to the differential amplifier and to the oscillator to input an output signal from the differential amplifier and the voltage signal from the oscillator which voltage signal serving as a reference signal. Additionally, a meter is connected to the lock-in amplifier to indicate a signal output from the lock-in amplifier.

It is preferable that the thus arranged searching instrument is further provided with the following-features so as to be further improved over the conventional techniques:

First, a power semiconductor element is used for an amplifier thereby to obtain a high frequency and high power output. Additionally, a container type ferrite core is used in the coil of the above-mentioned reference resonance circuit, and therefore the resonance circuit is prevented from being affected by circumferential lines of magnetic force thereby to improve the sensitivity and precision of the searching instrument.

In such a case, an output voltage V0' at the terminals of a capacitor of the resonance circuit is given by Eq. 7.

$$V_0' = \{(1/j\omega C)/R_0\} \times V_1 \quad (Eq. 7)$$

wherein $R_0$ is a direct current resistance of the coil; C is a capacity of the capacitor; $\omega$ is an angular frequency; j is the complex number; and $V_1$ is the input alternating current voltage.

Additionally, since the two resonance circuits used in the searching instrument are equally rated, the detection of the searching instrument is prevented from being affected by a temperature change. Accordingly, only a change in magnetic force upon approach of the sensor or probe to the reinforcing steel is output and amplified. Furthermore, by virtue of the lock-in amplifier, only a signal at a predetermined frequency is indicated in high sensitivity and precision by the meter.

Embodiments of reinforcing steel searching systems according to the principle of the present invention will be discussed hereinafter with reference to FIGS. 3 to 14.

Figure 3:
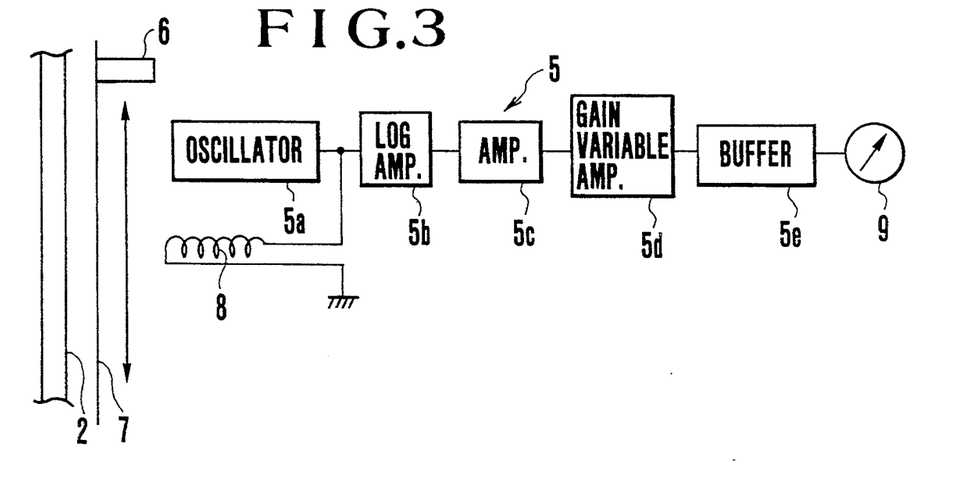
FIG. 3 is a circuit diagram of a first embodiment of a reinforcing steel searching system in accordance with the present invention.

FIG. 3 illustrates a first embodiment of the reinforcing steel searching system in accordance with the present invention, in which a non-resonance type reinforcing steel searching instrument 5 is used. In this embodiment, a permanent magnet 6 is used as a magnetizing device. First, the reinforcing steel 2 is magnetized under the action of the direct current magnetic field of the permanent magnet 6, and thereafter searching or detecting the reinforcing steel is carried out by using the non-resonance type searching instrument 5.

More specifically, the permanent magnet 6 is slidingly moved on the surface of a concrete 7 along a direction (indicated by an arrow) in which the reinforcing steel 2 is embedded in the concrete 7, so that the reinforcing steel 2 is magnetized with the magnetic flux radiated from the permanent magnet 6. Subsequently, the permanent magnet 6 is located sufficiently far from a measuring or detecting place, and then searching or detecting the reinforcing steel 2 is carried out by using the searching instrument 5.

The searching instrument 5 is arranged as follows: An oscillator 5a of the searching instrument 5 always outputs a voltage at a certain low frequency to be supplied to a sensor coil 8 (4) whose inductance changes by being approached to the reinforcing steel 2. An output voltage (proportional to the inductance of the sensor coil) from the sensor coil 8 is amplified by a logarithmic amplifier 5b, an amplifier 5c and a gain variable amplifier 5d. This amplification is carried out because the variation in inductance is generally small and required to be amplified. Additionally, the change of the inductance is large in case that the reinforcing steel is located near the sensor coil 8, while it is small in case that the reinforcing steel is located far from the sensor coil 8, so that the change of the inductance is non-linear relative to change in distance. In this regard, the logarithmic amplifier 5b is used to compress the change of the inductance. The amplifier 5c is used to accomplish a zero adjustment and a linear amplification. The gain variable amplifier 5d is used to make variable a resistance value of a feedback circuit by an outside change-over switch for the purpose of accomplishing an adjustment according to the diameter or thickness of the reinforcing steel 2. The buffer 5e is used to indicate an output from the amplifier 5d in a meter 9 which indicates the existence and location of the reinforcing steel.

Figure 4:
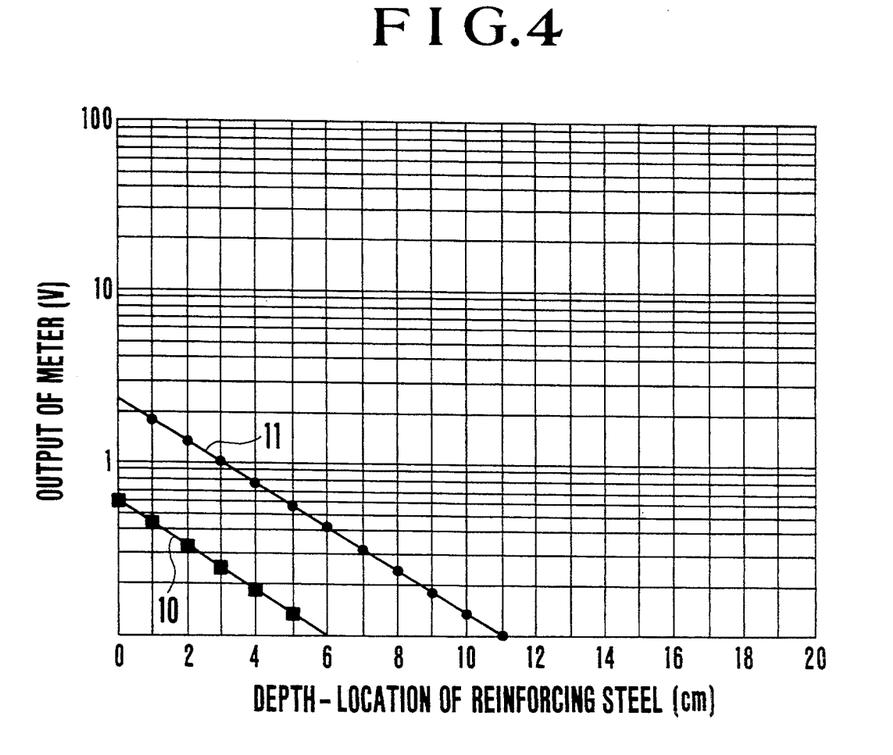
FIG. 4 is a graph showing an experimental measurement result of the system of FIG. 3.

The result of the searching for the reinforcing steel by the searching instrument 5 is shown in a logarithmic scale graph of FIG. 4 which represents a variation of relative output (voltage) of the meter 9 in terms of depth-location of reinforcing steel 2. A line 10 indicates the relative output of the meter in case that no magnetization to the reinforcing steel was made, whereas a line 11 indicates that magnetization to the reinforcing steel was made as discussed above with the non-resonance type searching instrument 5. It will be seen from FIG. 4 that the meter output in the case of employing the magnetization is several times that in the case of no magnetization. This demonstrates that the measuring or detection sensitivity and precision is about 5 times that in the conventional technique even upon incorporation of the magnetizing device 6 with the non-resonance type searching instrument 5.

Figure 5:
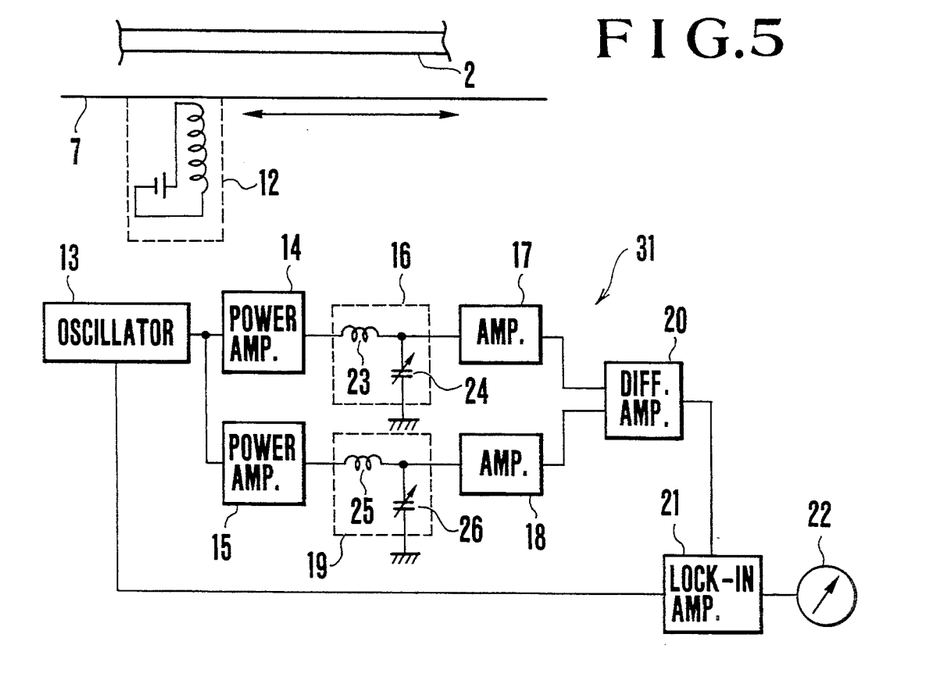
FIG. 5 is a circuit diagram of a second embodiment of the searching system in accordance with the present invention.

FIG. 5 illustrates a second embodiment of the reinforcing steel searching system according to the present invention, similar to the first embodiment of FIG. 3. In this embodiment, first the reinforcing steel 2 is magnetized under the action of the direct current magnetic field which is established by flowing direct current through a magnetizing coil 12. Thereafter, the searching or detecting the reinforcing steel 2 is carried out by using a resonance type reinforcing steel searching instrument 31 which includes first and second resonance circuits 16, 19. It will be understood that the magnetizing coil 12 is located far from the searching instrument 31 after magnetization of the reinforcing steel 2, thereby preventing the measurement or detection of the searching instrument from being affected by the magnetizing coil 12.

The searching instrument 30 of this embodiment is arranged as follows: A predetermined high frequency voltage signal generated from an oscillator 13 is input to the first and second resonance circuits 16, 17 through respective power amplifiers 14, 15. The first and second resonance circuits 16, 17 consist of the equally rated same element parts. The first resonance circuit 16 functions as a sensor and is connected between the power amplifier 14 and an amplifier 17 in series. The second resonance circuit 19 functions as a reference circuit and is connected between the power amplifier 15 and an amplifier 18 in Series. In this embodiment, the power amplifiers 14, 15 are equally rated. The resonance circuits 16, 19 are equally. The amplifiers 17, 18 are equally rated.

Subsequently, outputs from the two resonance circuit systems (including respectively the resonance circuits 16, 19) are input to a differential amplifier 20 in which the difference between the two ! outputs are amplified. An output from the differential amplifier 20 is input to a lock-in amplifier 21 which is directly connected to the oscillator 13 so that the predetermined high frequency voltage signal is supplied as a reference signal to the amplifier 21. An output from the lock-in amplifier 21 is input to a meter 22 and is limited only to the predetermined high frequency voltage signal, and then is indicated in the meter 22. The predetermined high frequency voltage signal used in this embodiment has a frequency from 10 KHz to 10 MHz.

The first resonance circuit 16 includes a coil 23 and a capacitor 24. The coil 23 is disposed in the probe which is, in this embodiment, small-sized and handy and arranged to be readily movable on the surface of the concrete under a manual operation or an automatic operation along a rail of a moving device (not shown). Additionally, the second resonance circuit 19 includes a coil 25 and a capacitor 26 and is encased together with other element parts other than the coil 23, in one or several containers as a main body of the searching instrument 31.

It is preferable that a FET (field effect transistor) or a power MOS(metal oxide semiconductor) FET is used as the power transistor 14. The power MOS FET may be replaced with a power transistor or a GTO (gate-turn-off) switch. It is to be noted that use of the power amplifier for a high power in such a searching instrument is characteristic. Additionally, it is preferable to use a container-shaped ferrite core (high in effect of increasing magnetic force) in the coil 25 of the reference resonance circuit 19.

Next, the feature and effect of the second embodiment searching instrument will explained. In this embodiment, the high frequency voltage signal generated by the oscillator 13 has, for example, a frequency of 100 KHz which is 6 to 10 times a corresponding frequency in the conventional technique using a resonance circuit. Use of such a high power at the high frequency is made possible by employing the MOS FET. This causes the sensor coil 23 in the probe to generate strong line of magnetic force which are considerably high as compared with the conventional technique, so that a change in the lines of magnetic force due to the existence of the reinforcing steel can be detected even if the reinforcing steel is embedded at a considerably deep location in the concrete, while largely improving the sensitivity of the detector or searching instrument 31.

Figure 6:
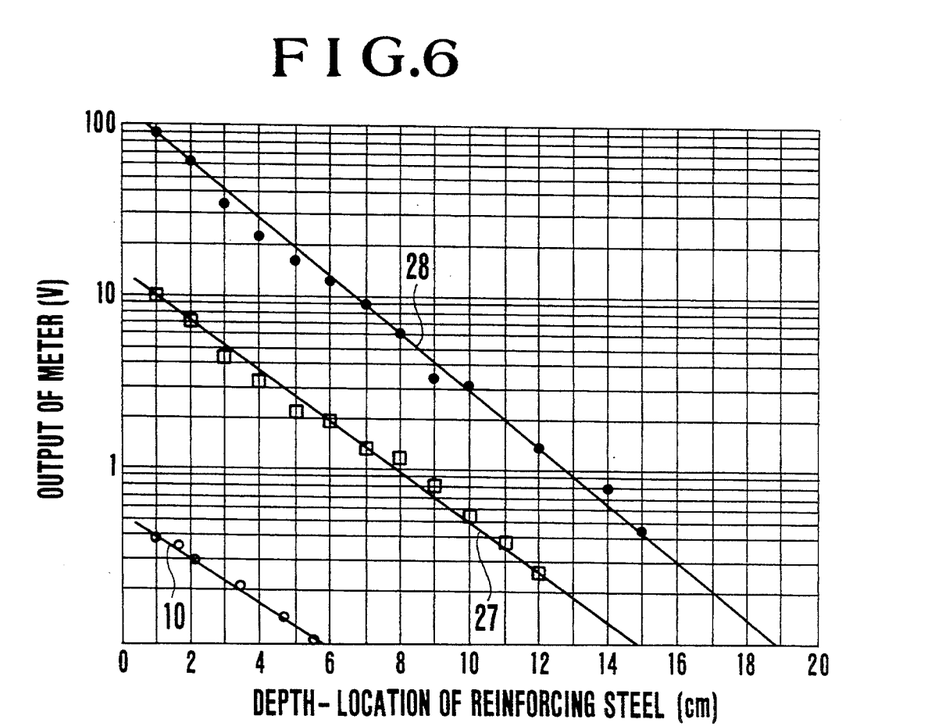
FIG. 6 is a graph showing an experimental measurement result of the system of FIG. 5.

The result of measurement by the searching instrument 31 is shown in a logarithmic scale graph of FIG. 6 which represents a variation in the relative output (voltage) of the meter 22 in terms of the depth-location of the reinforcing steel 2. A case (indicated by a line 28) of using the searching instrument 31 upon magnetization of the reinforcing steel provides a very high sensitivity of the searching or detection as compared with a case (indicated by a line 27) of using the searching instrument 31 without magnetization of the reinforcing steel and as compared with the conventional technique (indicated by a line 10) of using the third conventional technique using the searching instrument having a resonance circuit without magnetization of the reinforcing steel. Additionally, the graph of FIG. 6 demonstrates that the reinforcing steel 2 at the depth-location of 10 to 20 cm becomes searchable.

Figure 7:
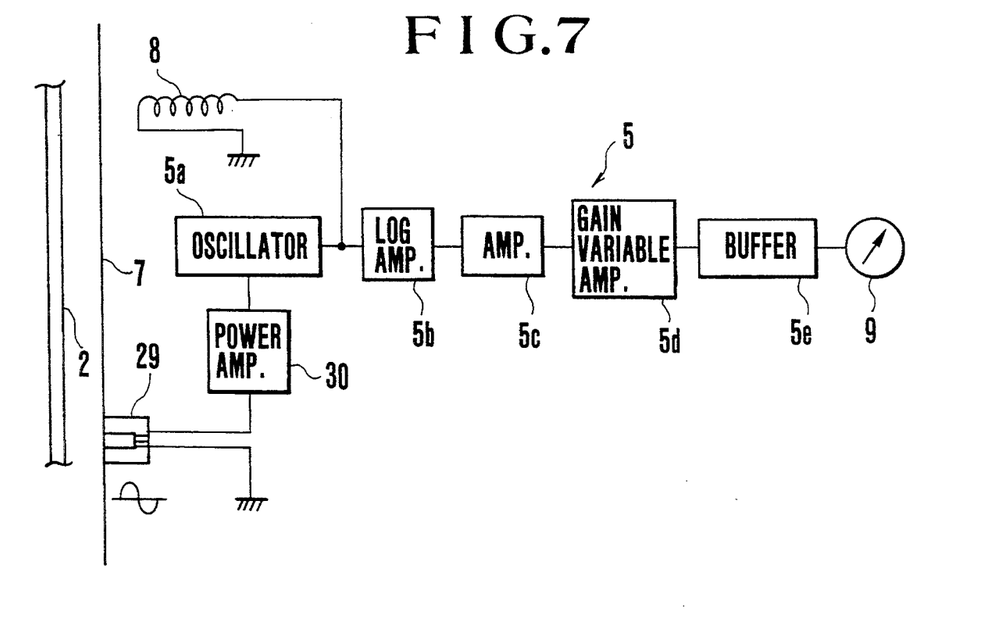
FIG. 7 is a circuit diagram of a third embodiment of the searching system in accordance with the present invention.

FIG. 7 illustrates a third embodiment of the reinforcing steel searching system in accordance with the present invention, which uses the non-resonance type searching instrument 5 and similar to the first embodiment of FIG. 3. In this embodiment, the reinforcing steel 2 magnetized by an alternating current magnetizing device 29 is searched or detected by the non-resonance type searching instrument 5.

The alternating current magnetizing device 29 is located on the surface of the concrete 7, facing the reinforcing steel 2. The magnetizing device 29 is adapted to be supplied from the oscillator 13 with a signal which is synchronized with and has the same frequency as the signal to be supplied to the sensor 8. Then, the magnetizing device 29 radiates a magnetic flux which causes the reinforcing steel 2 to be in a magnetized state. The thus magnetized reinforcing steel 2 is searched or detected by the searching instrument 5.

It is to be noted that, in this embodiment, the alternating currents of the magnetizing device 29 and the sensor coil 8 are the same in frequency and synchronized, so that detection of a signal from the reinforcing steel can be readily carried out while improving the sensitivity and precision of the detector or the searching instrument 5.

Figure 8:
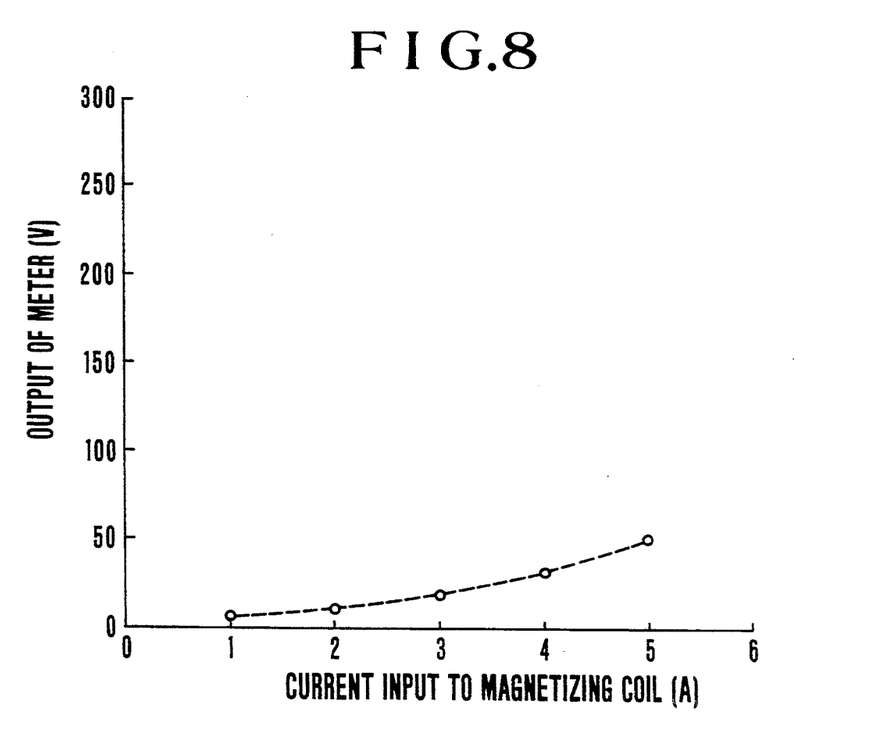
FIG. 8 is a graph showing an experimental measurement result of the system of FIG. 7.

The result of measurement of the searching instrument 5 is shown in FIG. 8 which represents a variation of a relative output (V) in the meter 22 in terms of a current input to the magnetizing coil (not shown) of the magnetizing device 29. According to the result, the relative output of the meter 9 was about zero when current input to the magnetizing device 29 was 2A, i.e, no magnetization of the reinforcing steel was made, while it was about 50 when the current input was 5A. This demonstrates that the sensitivity and precision of detection is increased 25 times that in the conventional technique. It will be understood that, in such a case using an alternating current magnetic field to magnetize the reinforcing steel, the magnetizing device 29 is supplied with an electric signal having a predetermined-frequency and a predetermined wave form such as a sine wave, chopping wave, square wave or pulse wave.

Figure 9:
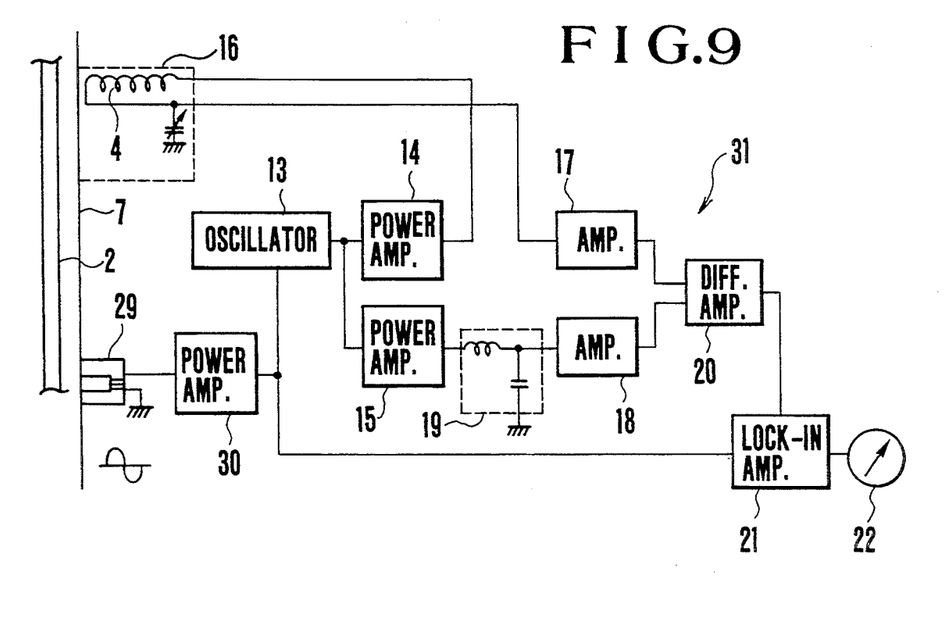
FIG. 9 is a circuit diagram of a forth embodiment of the searching system in accordance with the present invention.

FIG. 9 illustrates an embodiment of the reinforcing steel searching system of the present invention, similar to the second embodiment of FIG. 5 except for provision of the alternating current magnetizing device 29 used in the third embodiment of FIG. 7. In this embodiment, the alternating current magnetizing device 29 is supplied with a signal which is the same in frequency as and synchronized with a signal to be supplied to the resonance circuit systems including resonance circuits 16, 19. The reinforcing steel 2 is magnetized with the magnetic flux radiated from the alternating current magnetizing device 29, and thereafter searching or detecting the reinforcing steel 2 is carried out by the searching instrument 31. At this time, the alternating current magnetizing device 29 and the resonance circuit 16 (as the sensor) of the searching instrument 31 are separate from each other by such a distance that the magnetic fluxes respectively radiated from them are not functionally affected to each other. The reason why the alternating current magnetizing device 29 and the resonance circuit 16 are supplied with the same Frequency and synchronized signals from the same signal source is as follows: The magnetic fluxes radiated respectively from the resonance circuit 16 of the sensor 16 and from magnetized reinforcing steel 2 seem to coincide with each other in frequency and wave form, and therefore detection of the signal can be readily made even if noise is mixed with the magnetic flux so as to make difficult discrimination of the signal.

Figure 10:
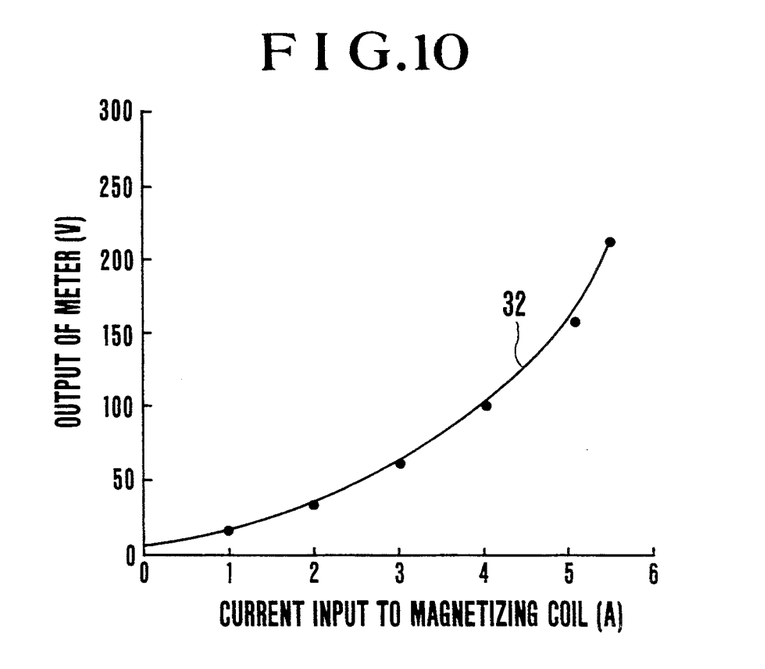
FIG. 10 is a graph showing an experimental measurement result of the system of FIG. 9.

The result of measurement or detection of the searching instrument 31 is shown in FIG. 10 which represents a variation of a relative output (V) of the meter 22 in terms of a current input to the magnetizing coil in the magnetizing device 29. As seen from a line 32 in FIG. 10, the relative output of the meter 22 is increased with an increase of current to be supplied to the alternating current magnetizing device 29. The graph of FIG. 10 shows that the relative output of 180 under the magnetization at 5A is about 35 times that of 10 under no magnetization or the conventional technique. This demonstrates that the fourth embodiment searching system 31 provides a reinforcing steel searching which is largely effective as compared with the conventional techniques. Additionally, this measurement result depicts not only an increase in relative output of the meter but also a large increase in searchable depth-location of the object reinforcing steel to a distance of 30 to 40 cm from the surface of the concrete.

Figure 11:
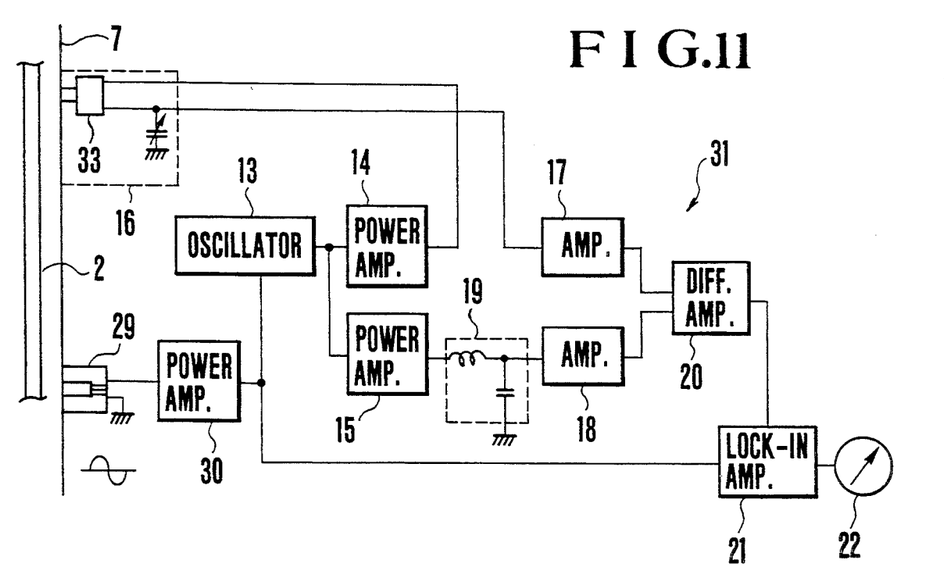
FIG. 11 is a circuit diagram of a fifth embodiment of the searching system in accordance with the present invention.
Figure 12:
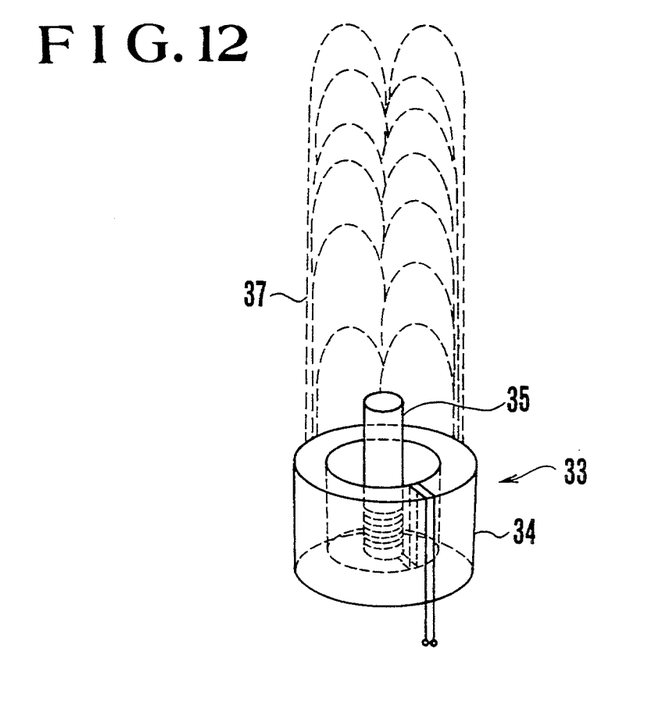
FIG. 12 is a schematic perspective view of a magnetic flux gun-type probe used in the system of FIG. 11.

FIG. 11 illustrates a fifth embodiment of the reinforcing steel searching system of the present invention, which is similar to the fourth embodiment with the exception that a so-called magnetic flux gun-type probe 33 is used in place of the sensor coil 4. As shown in FIG. 12, the magnetic flux gun-type probe 33 includes a rod-like central core 35 which is surrounded with a generally cylindrical peripheral core 34. The inner peripheral surface of the peripheral core 34 is spaced from the outer peripheral surface of the central core 35. The peripheral and central core 34, 35 are integral at their bottom with each other. A conductive wire is wound on the lower section of the central core 35 to form a coil (indicated by parallel broken lines in Fig. 12) which is connected at its terminals with the power amplifier 14 and the amplifier 17 through the capacitor as shown in FIG. 11. The peripheral core 34 is smaller in axial length than the central core 35.

With the thus arranged magnetic flux gun-type probe 33, the magnetic flux 37 radiated from the central core 35 is absorbed to the peripheral core 34 as shown in FIG. 12, in which the magnetic flux 37 is prevented from being unnecessarily scattered laterally and rearwardly so that the magnetic flux 37 is concentrated in the direction of the axis of the central core 35. It will be understood the coil is formed by winding a large amount of the conductive wire and is located in a space between the central and peripheral cores 35, 34, thus allowing a strong magnetic flux to be radiated only forward of the probe 33. Accordingly, the probe 33 functions like a gun for magnetic flux.

Figure 13:
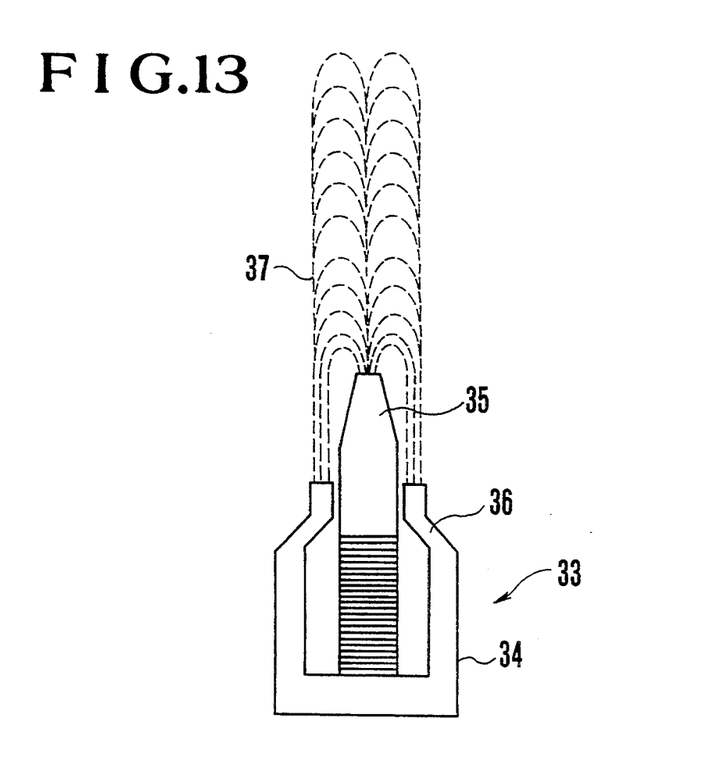
FIG. 13 is a schematic vertical sectional view of a modified example of the probe of FIG. 12.

FIG. 13 shows a modified example of the magnetic flux gun-type probe 33 which is similar to that of FIG. 12. In this example, the tip end section of the central core 35 is tapered or formed frustoconical. Additionally, the upper section of the peripheral core 36 is made so slender as to approach the outer peripheral surface of the central core 35. With this probe 33, the directivity of the magnetic flux 37 is further improved over that of the pro;be of FIG. 12, in which the magnetic flux from the central core 35 is strongly radiated straightly and forwardly.

Thus, the magnetic flux gun-type probes 33 of FIGS. 12 and 13 are largely improved in directivity and directional resolution of magnetic flux over the conventional techniques and the sensor coils 4, 8 of the above-discussed embodiments, so that the magnetic flux from the probe 33 can reach a considerably deep location of the concrete 7.

Figure 14:
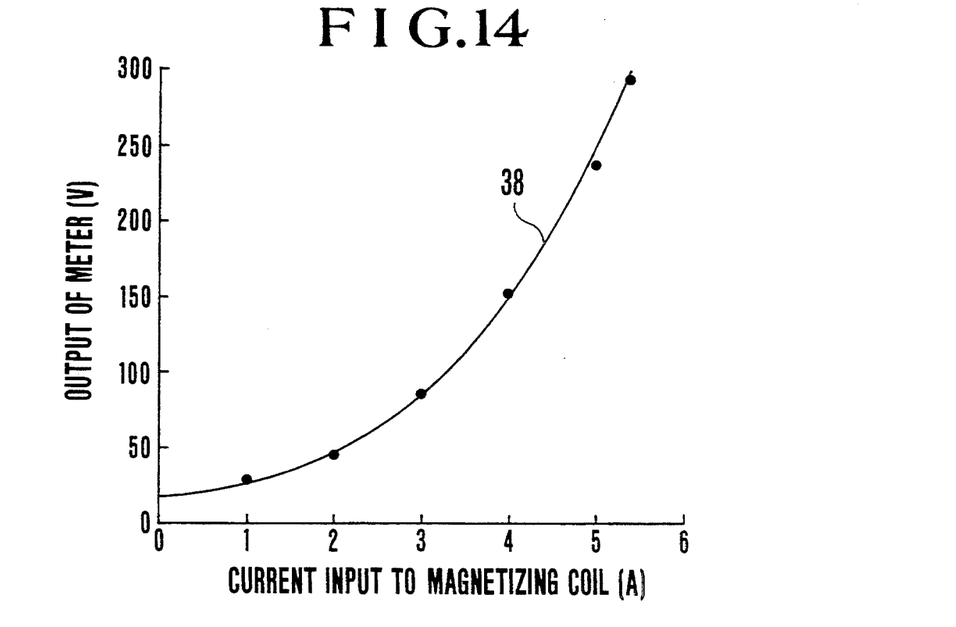
FIG. 14 is a graph showing an experimental measurement result of the system of FIG. 12.

The result of measurement or detection of the searching instrument 31 (with the probe 33 of FIG. 12) in FIG. 11 is shown in FIG. 14 which depicts a variation of a relative output of the meter 22 in terms of current (A) input to the magnetizing coil (not shown) of the magnetizing device 29. As indicated by a line 38 in FIG. 14, the relative output of the meter 22 reached about 300 which was about 30 times that (about 10) in case of no magnetization in which the input current is zero. This makes possible to search the reinforced steel located in a deep position of 50 to 60 cm from the surface of the concrete 7. In this connection, the searchable depth for the reinforcing steel 2 has been 5 to 6 cm in the conventional techniques. Thus, it will be understood that the searching system 31 with the magnetic flux gun-type probe 33 is largely improved over the conventional techniques and over the first to fourth embodiments.

What is claimed is:

1. A method of searching for and sensing reinforcing steel in reinforced concrete, comprising the steps of:
   magnetizing the reinforcing steel in the reinforced concrete with lines of magnetic force generated by a magnetic field from a magnetic means;
   sensing the lines of magnetic force radiated from the magnetized reinforced steel to detect the existence of and the condition of the reinforcing steel in the reinforced concrete using a reinforcing steel searching instrument having a coil for sensing a magnetic force,
   said step of sensing the lines of magnetic force including the step of positioning the magnetic means remote from said searching instrument, and
   said step of magnetizing the reinforcing steel comprising forming the lines of magnetic force by using an alternating current magnetic field;
   said step of magnetizing the reinforcing steel comprising generating a first electrical signal by an oscillator, and outputting said first electrical signal to generate said alternating current magnetic field;
   said step of sensing the lines of magnetic force comprising generating a second electrical signal by the oscillator, said second electrical signal having the same frequency as and synchronized with said first electrical signal.

2. A system for searching and sensing a reinforcing steel in a reinforced concrete, comprising:

means for magnetizing the reinforcing steel in the reinforced concrete with lines of magnetic force generated by a magnetic field; and means for sensing the lines of magnetic force radiated from the magnetized reinforcing steel to detect an existence and a condition of the reinforcing steel in the reinforced concrete, said sensing means including a coil for sensing a magnetic force, said magnetizing means being positioned remote from said sensing means, said sensing means includes an oscillator connected to said magnetic field sensing coil, said oscillator generating a voltage signal to be output to said magnetic force sensing coil.

3. A system for searching and sensing a reinforcing steel in a reinforced concrete comprising:

means for magnetizing the reinforcing steel in the reinforced concrete with lines of magnetic force generated by a magnetic field; and means for sensing the lines of magnetic force radiated from the magnetized reinforcing steel to detect an existence and a condition of the reinforcing steel in the reinforced concrete, said sensing means including a coil for sensing a magnetic force, said magnetizing means being positioned remote from said sensing means, said magnetizing means includes means for generating an alternating current magnetic field, said sensing means includes an oscillator connected to said magnetic field sensing coil, said oscillator generating a first voltage signal to be output to said magnetic force sensing coil, and a resonance circuit connected to said oscillator and including said magnetic force sensing coil, said resonance circuit inputting said first voltage signal having a frequency around a resonance frequency, from said oscillator and outputting a second voltage signal representing a change in inductance caused upon an approach of said magnetic force sensing coil to the reinforcing steel.

4. A system for searching and sensing a reinforcing steel in a reinforced concrete, comprising:

means for magnetizing the reinforcing steel in the reinforced concrete with lines of magnetic force generated by a magnetic field; and means for sensing the lines of magnetic force radiated from the magnetized reinforcing steel to detect an existence and a condition of the reinforcing steel in the reinforced concrete, said sensing means including a coil for sensing a magnetic force, said magnetizing means being positioned remote from said sensing means, said sensing means includes an oscillator for generating a predetermined high frequency voltage signal, a first resonance circuit connected in series with said oscillator and including said magnetic force sensing coil and a first variable capacitor, said first resonance circuit being adapted to input said voltage signal having a frequency around a resonance frequency and output a second voltage signal representative of a change in inductance generated upon approach of said magnetic force sensing coil to the reinforcing steel, a second resonance circuit connected in series with said oscillator and in parallel with said first resonance circuit, said second resonance circuit including a coil and a second variable capacitor which are equally rated respectively with said magnetic force sensing coil and said first variable capacitor, a differential amplifier connected to said first and second resonance circuits to calculate a difference in output between said first and second resonance circuits, a lock-in amplifier connected to said differential amplifier and to said oscillator to input an output signal from said differential amplifier and said voltage signal from said oscillator, said voltage signal serving as a reference signal, and means for indicating a signal output from said lock-in amplifier.

5. A method of searching for and sensing reinforcing steel in a concrete structure having reinforcing steel incorporated therein and spaced from a surface of said structure, comprising the steps of:

magnetizing the reinforcing steel in the reinforced concrete with a source of a magnetic field, and then removing said source from influencing the magnetic field of said reinforcing steel, whereby lines of magnetic force extend from a surface of said structure without magnetic influence from said source;

positioning a coil at a position adjacent said surface whereby the inductance of said coil at said position is dependent upon said lines of force extending from said structure; and applying an oscillatory voltage to said coil and measuring the resultant voltage across said coil, Whereby said resultant voltage is dependent upon the relative location of said reinforcing steel with respect to said surface.

6. The method of claim 5 further comprising connecting a capacitor to said coil to form a resonant circuit.

7. A method of searching for and sensing reinforcing steel in a concrete structure having reinforcing steel incorporated therein and spaced from a surface of said Structure, comprising the steps of:

magnetizing the reinforcing steel in the reinforced concrete with a source of an oscillatory magnetic field, whereby lines of magnetic force extend from a surface Of said structure;

positioning a coil at a position adjacent said surface whereby the inductance of said coil at said position is dependent upon said lines of force extending from said structure; and applying an oscillatory voltage to said coil of the same frequency and synchronized with said oscillatory magnetic field, and measuring the resultant voltage across said coil, whereby said resultant voltage is dependent upon the relative location of said reinforcing steel with respect to said surface.

8. The method of claim 7 further comprising connecting a capacitor to said coil to form a resonant circuit.

9. A system for searching and sensing a reinforcing steel in a reinforced concrete structure, comprising:

a source of a direct magnetic field having a first position at which the direct magnetic field magnetizes said reinforcing steel in reinforced concrete and a second position at which said direct magnetic field does not magnetize said reinforcing steel, whereby magnetic lines of force extend from a surface of said structure when said reinforcing steel has been magnetized by said source;

a coil movable to a position adjacent said surface to a position at which the inductance thereof is influenced by said magnetic lines of force when said source is in said second position;

a source of an oscillatory voltage;

means applying said oscillatory voltage to said coil; and means for measuring the resultant voltage across said coil, whereby said resultant voltage is a function of the depth of said reinforcing steel in said structure, from said surface.

10. The system of claim 9 further comprising a capacitor connected in parallel with said coil to form a resonant circuit.

11. A system for searching and sensing a reinforcing steel in a reinforced concrete structure, comprising:

a source of an oscillatory magnetic field positionable to magnetize said reinforcing steel, whereby magnetic lines of force extend from a surface of said structure in response to magnetization of said reinforcing steel by said source;

a coil movable to a position adjacent said surface to a position at which the inductance thereof is influenced by said magnetic lines of force;

a source of an oscillatory voltage of the same frequency as and synchronized with said oscillatory magnetic field;

means applying said oscillatory voltage to said coil; and means for measuring the resultant voltage across said coil, whereby said resultant voltage is a function of the depth of said reinforcing steel in said structure, from said surface.

12. The system of claim 11 further comprising a capacitor connected in parallel with said coil to forms resonant circuit.

13. A method for search for and sensing reinforcing steel in a reinforced concrete, comprising:

magnetizing reinforcing steel in reinforced concrete with lines of magnetic force generated by a magnetic field, said lines of magnetic force generated by at least one of a permanent magnet; a direct current magnetic field; and an alternating current magnetic field produced by a first electrical signal generated and output from an oscillator; and upon completion of magnetizing said reinforcing steel sensing the lines of magnetic force radiated from the magnetic reinforcing steel to detect an existence and a condition of the reinforcing steel in the reinforced concrete by using a reinforcing steel searching instrument having a coil for sensing a magnetic force, the inductance of said coil dependent upon lines of said force extending from any reinforcing steel and said coil outputting a voltage dependent upon said inductance.

14. In the method as claimed in claim 13, said searching instrument includes an oscillator connected to said magnetic force sensing coil, said oscillator generating a voltage signal to be output to said magnetic force sensing coil.

15. In the method as claimed in claim 13, said searching instrument including said oscillator connected to said magnetic force sensing coil, and a resonance circuit connected to said oscillator and including said magnetic force sensing coil, said resonance circuit inputting said first electrical signal having a frequency around a resonance frequency, from said oscillator and outputting a second electrical signal representing a change in inductance caused upon an approach of said magnetic force sensing coil to the reinforcing steel.

16. In the method as claimed in claim 15, said oscillator supplying a third electrical signal having the same frequency as and synchronized with said first electrical signal.

17. In the method as claimed in claim 13, said searching instrument including an oscillator for generating a predetermined high frequency voltage signal, a first resonance circuit connected in series with said oscillator and including said magnetic force sensing coil and a first variable capacitor, said first resonance circuit being adapted to input said voltage signal having a frequency around a resonance frequency and output a second voltage signal representative of a change in inductance generated upon approach of said magnetic force sensing coil to the reinforcing steel, a second resonance circuit connected in series with said oscillator and in parallel with said first resonance circuit, said second resonance circuit including a coil and a second variable capacitor which are equally rated respectively with said magnetic force sensing coil and said first variable capacitor, a differential amplifier connected to said first and second resonance circuits to calculate a difference in output between said first and second resonance circuits, a lock-in amplifier connected to said differential amplifier and to said oscillator to input an output signal from said differential amplifier and said voltage signal from said oscillator, said voltage signal serving as a reference signal, and means for indicating a signal output from said lock-in amplifier.

18. In the method as claimed in claim 17, said searching instrument including first and second equally rated power amplifiers, said first power amplifier being connected in series between said oscillator and said first resonance circuit, said second power amplifier being connected in series between said oscillator and said second resonance circuit.

19. In the method as claimed in claim 18, said searching instrument further including a first and second amplifier, said first amplifier being connected in series between said first resonance circuit and said differential amplifier, said second amplifier being connected in series between said second resonance circuit and said differential amplifier.

20. In the method as claimed in claim 17, wherein said voltage signal has a frequency ranging from 10 khz to 10 Mhz.

21. In the method as claimed in claim 17, wherein said oscillator is a crystal oscillator.

22. In the method as claimed in claim 18, wherein each power amplifier includes a semiconductor element.

23. In the method as claimed in claim 17, wherein said coil of said second resonance circuit includes a ferrite core.

24. The method as claimed in claim 13, wherein a second electrical signal is generated by an oscillator, said second electrical signal having the same frequency as and being synchronized with said first electrical signal.

25. In the method as claimed in claim 13, said searching instrument including a probe including a generally cylindrical peripheral core made of a magnetic material, a rod-like central core which is connected with said peripheral core, said central core being larger in axial length than said peripheral core, an electrically conductive coil formed around said central core, said coil corresponding to said magnetic force sensing coil.

26. In the method as claimed in claim 25, said rod-like central core being generally cylindrical and coaxial with said peripheral core.

27. In the method as claimed in claim 25, said central core being tapered at its free tip end section.

28. In the method as claimed in claim 27, said peripheral core comprising a generally cylindrical free end section located near said tapered tip end section, said free end section of said peripheral core being generally frustoconical so as to approach a peripheral surface of said central core.

* * * * *